(12) United States Patent
Unger (10) Patent No.: US 9,265,258 B2
(45) Date of Patent: Feb. 23, 2016

(54) READIED IN SITU GLYPHOSATE HERBICIDE SOLUBLE POWDER COMPOSITION AND ITS PREPARATION PROCESS

(71) Applicant: ALLVET QUIMICA INDUSTRIAL LTDA., Londrina, Parana (BR)

(72) Inventor: Thomas Alfred Unger, Sao Paulo (BR)

(73) Assignee: ALLVET QUIMICA INDUSTRIAL LTDA., Londrina, Parana (BR)

( * ) Notice: Subject to any disclaimer, the term of this patent is extended or adjusted under 35 U.S.C. 154(b) by 251 days.

(21) Appl. No.: 13/916,316

(22) Filed: Jun. 12, 2013

(65) Prior Publication Data

US 2013/0274108 A1    Oct. 17, 2013

Related U.S. Application Data

(63) Continuation of application No. PCT/BR2011/000257, filed on Aug. 2, 2011.

(51) Int. Cl.
*A01N 57/20* (2006.01)
*C05G 3/02* (2006.01)

(52) U.S. Cl.
CPC . *A01N 57/20* (2013.01); *C05G 3/02* (2013.01)

(58) Field of Classification Search
CPC ....... A01N 57/20; A01N 25/30; A01N 25/12; A01N 59/00; A01N 2300/10; C05G 3/02
See application file for complete search history.

(56) References Cited

U.S. PATENT DOCUMENTS

| | | |
|---|---|---|
| 5,118,338 A | 6/1992 | Moller |
| 5,591,443 A | 1/1997 | Heinicke |
| 5,652,197 A | 7/1997 | Claude et al. |
| 6,228,807 B1 | 5/2001 | Kuchikata et al. |
| 2003/0100449 A1* | 5/2003 | Maeda et al. ............ 504/127 |
| 2009/0318294 A1* | 12/2009 | Malec et al. ............ 504/206 |
| 2011/0105330 A1 | 5/2011 | Leite |

FOREIGN PATENT DOCUMENTS

| | | |
|---|---|---|
| EP | 498145 | 11/1995 |
| WO | 2010053385 A1 | 5/2010 |
| WO | WO-2011/029561 A2 * | 3/2011 |

OTHER PUBLICATIONS

International Search Report issued for corresponding International Patent Application PCT/BR2011/000257 mailed Sep. 5, 2011.

* cited by examiner

*Primary Examiner* — Ali Soroush
(74) *Attorney, Agent, or Firm* — Myers Wolin, LLC (57) ABSTRACT

This invention relates to a readied in situ glyphosate herbicide soluble powder composition of high efficiency and low toxicity useful for killing and/or controlling weeds. This invention is also related to a process to prepare the said composition. It is another object of this invention to provide a new composition that consists of a soluble powder herbicide formulation characterized by a very narrow range of specific ingredients of composition, which optimizes the formulation efficiency and minimizes the cost and toxicity to man, to the environment and to the crop being treated. The required amount of glyphosate that needs to be applied on the field is reduced by 30% when compared to the commercially standard liquid solution.

7 Claims, 1 Drawing Sheet

READIED IN SITU GLYPHOSATE HERBICIDE SOLUBLE POWDER COMPOSITION AND ITS PREPARATION PROCESS

CROSS-REFERENCE TO RELATED APPLICATIONS

This is a continuation of PCT/BR2011/000257, filed Aug. 2, 2011, the contents of which are incorporated by reference herein.

FIELD OF THE INVENTION

This invention relates to a glyphosate water soluble powder herbicide composition useful for killing and/or controlling weeds, the distinguishing characteristics of the composition being an unusual high efficacy, low toxicity and low cost. This invention also relates to a process to prepare the said powder composition so as to obtain a single packaged readied in situ powder composition which dissolves in the water tank being transformed in a liquid composition appropriate for spraying on the field.

Pesticides are toxic substances. Therefore there is a worldwide drive to reduce the amount of pesticides applied on the field. This can only be achieved by an increase of pesticide efficacy so that less product needs to be applied on the field without however, increasing pesticide cost so as not to increase the cost of food. It is an objective of this invention to provide a low cost but more efficient new herbicide composition, which aims to meet these objectives.

The applicant research has covered different technical aspects. First, the applicant developed a judicious selection of the modifying-activating adjuvants and their optimal dosage. After intensive efforts, the applicant determined, among the uncountable modifying-activating adjuvant substances commonly used in herbicides formulations, which amongst them would be the most cost effective and least toxic.

Furthermore, the applicant determined the precise amount of each ingredient of the formulation so as to attain a greatly increased efficacy thereby reducing the required amount of glyphosate acid to be applied by the farmer on the field. The applicant then determined the physical form of the herbicide formulation in order for the formulation to be stable. Another objective for cost reduction was that the preparation of the soluble glyphosate salt should be in situ in the water tank avoiding the prior preparation of the salt by a separate operation. Finally the applicant developed a manufacturing process so as to achieve the lowest possible cost for the final product.

Consequently, the present invention discloses a new and improved readied in situ glyphosate water soluble powder herbicide composition, which is the result of great effort, intensive research and extensive tests in the field. The new composition consists of a soluble powder herbicide formulation characterized by a very narrow range of specific ingredients of composition, which optimize the formulation efficiency and minimize the cost and toxicity to man, to the environment and to the crop being treated.

Surprisingly, according to the subject matter disclosed in the present invention, the amount of glyphosate that needs to be applied on the field is reduced by 30% when compared to the standard 360 g/l liquid solution formulation. It must be understood that said standard liquid solution is ROUNDUP® a well-known commercial formulation sold by Monsanto.

Consequently, the soluble powder glyphosate herbicide formulation disclosed by the applicant invention is 30% more efficient than the standard formulation. The final result is a cost reduction per hectare treated of 35% to 40% when compared with the standard formulation. Moreover, 30% of this cost reduction is due to the incorporation of the optimal amount of an activator in combination with an appropriate surfactant, corresponding to a 30% reduction in the amount of glyphosate, which needs to be applied on the field. The remaining 5% to 10% of cost reduction is due to a judicious selection and optimal dosage of the other components, particularly, the surfactant, the physical form of the formulation and the fact that the formulation does not require a previous preparation of the soluble salt of glyphosate by a separate operation.

It is a further object of this invention to provide a low cost manufacturing, packing, handling, storage and shipping herbicide formulation which includes a low toxicity surfactant.

It should be understood that the present invention discloses a new product since it provides a new herbicide composition which consists of a single packaged readied in situ composition, in the form of a specific powder formulation, which comprises glyphosate along with modifying-activating adjuvants with a much higher efficacy than other known glyphosate powder formulations, having at the same time the advantage that the soluble salt of glyphosate is prepared upon use directly in the water tank and not previously in a separate facility.

The very narrow range of specific ingredients of composition is what makes this new powder formulation a product which presents a 30% increase in efficacy when compared to other known formulations, particularly the standard 360 g/liter liquid formulation, which does not require previous preparation of the soluble glyphosate salt by a prior separate operation, has a low toxicity, has a high content of the glyphosate active ingredient, and is more economical to manufacture, transport, handle, store and package, all together in a single readied in situ mixture which constitutes a unique novel product not described in the literature nor commercially existent and which will have a most beneficial effect on the environment and the cost of food.

It is another subject of this invention to disclose a new herbicide composition which is a single package readied in situ composition for the farmer.

BACKGROUND OF INVENTION

Farmers use many agrochemicals to protect or improve their crops. Herbicides are the biologically active ingredients commonly used to control weeds or undesired vegetation in agriculture.

Glyphosate, N-(phosphonomethyl)-glycine, is one of the most frequently applied herbicides for non-selective control of weeds. It is present in a well-known commercial composition known mainly under the registered trademark ROUNDUP® sold by Monsanto but is also sold under many other trademarks by many other companies.

Glyphosate is a broad spectrum, post emergence herbicide commonly used in the domestic, industrial and agricultural markets for weed control.

Glyphosate is well known in the art as an effective herbicide and is by far the main pesticide applied worldwide. It is used on nearly all crops against approximately 300 different types of weeds. Glyphosate represents in value approximately 15% of the entire pesticide market.

Glyphosate may be formulated in a wide variety of liquid and solid compositions designed to cover a range of applications. Liquid formulations are by far the most common, because they can include liquid surfactants, which are less expensive than solid surfactants and can be incorporated directly into the glyphosate liquid formulations. Currently, liquid fatty amine ethoxylated derivatives are the main liquid surfactants used for glyphosate, but they are known for their toxicity.

Solid formulations have an advantage over liquid formulations in so far as they can present a higher concentration of the glyphosate active ingredient which increases their advantage over liquid formulations regarding the amount of product to be transported and therefore packing, freight, handling and storage costs. In addition, only using a solid formulation is it possible to prepare the glyphosate soluble salt in situ in the water tank. Consequently, researchers tend to favor the development of new glyphosate formulations in the form of a granule or powder.

The manufacture of a powder requires much less investment than that of a granule. There are, therefore, strong reasons for developing a formulation in the form of a powder All herbicide formulations include a surfactant to lower surface tension and spread the pesticide on the leaf. Usually, solid formulations use solid surfactants which can be incorporated directly into a powder or granule. Most of these solid surfactants are much more expensive and less efficient with glyphosate than the liquid fatty amine derivatives currently used in most glyphosate liquid formulations.

One of the objectives of this invention was to be able to incorporate a highly efficient liquid surfactant, which has a low toxicity, is inexpensive, and is fully compatible and appropriate for use with the other components of the formulation, all in a readied in situ powder formulation. However the incorporation of a liquid surfactant in a readied in situ powder formulation is not a simple procedure. Therefore, the exclusion of these solid surfactants created an obstacle to the development of the powder formulation.

So, according to the instant invention, the presentation form for the composition as a readied in situ water soluble powder incorporating a highly efficient, low toxicity liquid surfactant, is an alternative to state of the art formulations and brings notable advantages, as one can see in the present description.

When glyphosate is applied to selected weeds it acts by interrupting protein formation, which is the basic component of living cells, thus killing the plant.

Protein synthesis in plants proceeds in three steps: (i) reduction of nitrates to nitrites followed by reduction of nitrites to ammonia (ii) formation of amino acids (iii) formation of proteins from amino acids via DNA/RNA replication.

Glyphosate acts in step (ii). A key reaction in the multi stage synthesis of the essential aromatic amino acids, phenylalanine and tryptophan, is the reaction between Shikimate-3-Phosphate and Phospho-Enol Pyruvate (PEP) to form a compound known as EPSP (5-enolpyruvylshikimate-3-phosphate). This reaction is catalyzed by an enzyme known as EPSPS (5-enolpyruvylshikimate-3-phosphate synthase). Glyphosate and PEP have a similar molecular structure so the fact that glyphosate mimics PEP leads EPSPS to take up glyphosate instead of PEP thereby inhibiting its action and interrupting the reaction sequence.

EPSPS does not present an accentuated preference for glyphosate or PEP so that the success of glyphosate is achieved by the sheer number of molecules of glyphosate which must crowd out a smaller number of molecules of PEP. Therefore it is vital to get the largest amount of glyphosate into the leaf in the shortest possible time. While this is an important consideration for all herbicides, it is particularly so for glyphosate the effective action of which depends exclusively upon the amount of product introduced into the leaf. If more glyphosate is made to enter the plant in a shorter time one can reduce the amount of glyphosate applied on the field.

In order to kill the plant, glyphosate must first get through the leaf cuticle which covers both sides of the leaf. Resistance to diffusion of the pesticide through the cuticle is due to an outer layer of wax as well as to waxes embedded in the cuticle itself.

The purpose of the cuticle is to avoid loss of water which would lead to desiccation of the plant. Since the cuticle avoids water from getting out, it also avoids water and therefore water soluble pesticides from getting in.

There is a growing trend to combine herbicides with adjuvants which increase the efficacy of the herbicide. The spray mixture for herbicide application contains an effective amount of known herbicide along with adjuvants and water. Sometimes the adjuvant must be added to ensure optimum performance of the actives in a variety of conditions which may otherwise inhibit it, for example, hard water, high temperatures, and poor growing conditions. The adjuvants, generally, are added to the herbicide spray mixture to enhance post emergence weed control and/or to reduce spray drift during herbicide application.

The types of substances which are used as adjuvant include plants nutrients, particularly, ammonium salts, wetting agents, spray drifts retardants, lipophilic solvents, surfactants and emulsifiers Typically, the addition of ammonium ions by the introduction of an ammonium salt in the composition enhances the effect of glyphosate, possibly by accelerating the rate of diffusion through the cuticle.

Glyphosate is a highly polar structure. Because of the low dissociation constant ($pK_a$=0.8) one of the protons of the acid migrates readily to the nitrogen atom leaving a negative charge on the phosphonic acid and a positive charge on the nitrogen atom, thus forming the zwitterion, which is described by the equation:

Hydrophilic ions such as the zwitterion have difficulty diffusing through waxes and their rate of diffusion is much lower than for a non-dissociated molecule.

The addition of ammonium ions in the formulation by the introduction of an ammonium salt such as for instance ammonium sulfate leads to a less dissociated compound and consequently to a faster rate of diffusion. This faster rate of diffusion signifies that more glyphosate enters the plant in a shorter period of time which leads to a reduction in the amount of glyphosate required on the field, Because of this effect, ammonium sulfate is often referred to as being an activator for glyphosate. Since ammonium sulfate is an inexpensive fertilizer, the combined exposure of weeds to this fertilizer and glyphosate can substantially increase the efficacy of the active molecule at a very low cost.

Considering that ammonium ions facilitate diffusion through the cuticle leading to a much faster rate of entry of glyphosate into the plant; and that there exists a specific necessary amount of glyphosate required to inhibit EPSPS, the researches of the instant invention surprisingly discovered that there exists a specific proportion of ammonium ions to glyphosate acid which leads to a maximum efficacy of the formulation supplied from a solution containing less glyphosate. So, according to the present application, despite the fact that many glyphosate herbicides use an ammonium salt as activator, only the determination of the optimum amount—defined as being the smallest amount of ammonium salt which leads to the maximum gain of efficacy—opens the possibility of designing a solid powder formulation with a very narrow amount of specific ingredients of composition so as to present simultaneously all the desired properties of greatly increased efficacy, in situ preparation of the soluble glyphosate salt in the water tank, and a high content of the glyphosate active ingredient.

One can conclude that the faster rate of glyphosate diffusion through the leaf cuticle occurs in herbicide formulations which contain ammonium ions, and that, this faster rate of diffusion leads to a reduction in the amount of glyphosate required on the field, in order to produce the improved results. One can further conclude from the zwitterion dissociation equilibrium that there is an optimum amount of ammonium ions to be used in order to minimize dissociation of the glyphosate molecule.

Any inorganic salt which acts as a supplier of ammonium ions can be used, such as, ammonium nitrate, ammonium chloride, ammonium carbonate, ammonium bicarbonate, ammonium phosphate or ammonium sulfate. Ammonium nitrate is less attractive being commonly used as an oxidizing agent in explosives. Also it requires the use of more product per ammonium ion. Ammonium chloride is more expensive than ammonium sulfate and has the disadvantage that the chloride ion will presumably end up as sodium chloride and it is undesirable to salt the soil. Ammonium carbonate is much more expensive than the other salts. For these reasons the applicant of the present invention selected ammonium sulfate as the preferable activator. Ammonium phosphate is a valid alternative.

Ammonium sulfate's main use is as an inexpensive fertilizer. The combined exposure of weeds to this fertilizer and glyphosate can substantially increase the efficacy of glyphosate. This fertilizer accelerates the translocation of the glyphosate herbicide within the weeds, increasing the kill rate of the weeds. The use of an inexpensive fertilizer can increase the efficacy of glyphosate at a minimum cost. However, the use of ammonium sulfate is problematic because its solubility in water varies with changes in water quality. Water temperatures, hardness and mineral content all affect the mixing of ammonium sulfate in the spray mixture. This unpredictable solubility has been problematic for farmers who need to apply glyphosate to kill weeds in a crop.

Therefore typically, commercial glyphosate formulations contain an adjuvant surfactant to provide increased spray retention on the leaf surface and increase herbicide absorption into the plant. However, a surfactant alone often is not able to increase herbicide efficacy, especially when hard or very hard water is used as a spray carrier.

In addition, the surfactant in commercial glyphosate formulations is often not sufficient to optimize efficacy and does not prevent antagonism from spray-carrier cations. Thus, a combination of a surfactant and ammonium salts is required. Ammonium sulfate overcomes the antagonistic effect of sodium, calcium and magnesium ions in hard water. Furthermore, ammonium ions from an ammonium salt such as ammonium sulfate, provided that they are present in an adequate amount, greatly increase glyphosate herbicide absorption. The mixture of an appropriate surfactant and ammonium sulfate is a beneficial combination that increases the efficacy of many herbicides, particularly glyphosate.

Most surfactant adjuvants sold for use with herbicides are physically compatible with ammonium sulfate when diluted with water in a sprayer tank. However, specific surfactants are required for maximum efficacy when used in combination with ammonium sulfate and the choice of the wrong surfactant can reduce efficacy. Thus the effect of ammonium sulfate is markedly dependent on the type of surfactant. There are a large number of surfactant products available, so it is difficult to establish which is the most effective compound to be used with ammonium sulfate.

The preferential formulation is understood as one which could attend to all the commercial and environmental requirements, such as, maximum reduction in glyphosate amount associated with the highest activity, low toxicity and cost effectiveness. For solid formulations, researchers have used mainly solid surfactants which are easily incorporated in a powder or granule but are generally more expensive and less efficient than liquid fatty amine derivatives commonly used in glyphosate liquid formulations so that until now, they did not find the ideal surfactant for a glyphosate powder formulation containing ammonium sulfate.

There are two pathways for the glyphosate penetration into the plant leaf, either through the stomata or by diffusion through the outer layer of wax which covers the cuticle and through the cuticle itself.

Entry through the stomata can only occur during the short period of time that follows the application of the formulation and while there is still a liquid on the surface of the leaf, that is, before evaporation of the solvent. Furthermore, surface tension is usually not low enough to allow for penetration through the stomata. Therefore, by far the main route for entry and translocation of glyphosate is by diffusion. The main resistance to diffusion is the waxes embedded in the cuticular layer, and to a lesser degree the wax crystals and wax film embedded in the cuticle. So, these conditions represent the main technical features that researchers have to overcome in order to develop ideal herbicidal compositions.

According to U.S. Pat. No. 5,591,443, amide surfactants are described as suitable membrane transfer agents. Said patent discloses a proteinaceous insecticidal composition for combating insects. The composition consists of a synergistic combination of a unique type of protein prepared from casein with an effective critical amount of this membrane transfer agent that will translocate this unique protein across normally impermeable membrane barriers. Preferred membrane transfer agents are N-monoalkanolamine or N-dialkanolamine fatty acid amide and N-propylbetaine fatty acid amide.

It should be observed that this type of surfactant is used in order to transfer proteinaceous extracts across normally impermeable insect membranes. Moreover, the U.S. Pat. No. 5,591,443 patent does not intend to kill weeds nor to develop a single readied in situ soluble powder glyphosate herbicide formulation characterized by a very narrow amount of a specific ingredients of composition, which optimize formulation efficiency, minimize costs and toxicity.

So, considering the remarkable effect of the surfactant agent with ammonium sulfate present in the applicant invention, one cannot consider obvious the choice of these substances to act as a surfactant suitable for the improved herbicide powder composition.

According to EP 498.145, a solid phytoactive glyphosate composition is provided. The solid composition comprises: (a) N-phosphonomethylglycine in the form of a salt or the free acid; (b) a surfactant comprising an alkyl glycoside or alkyl polyglycoside; and, (c) an agriculturally acceptable inorganic ammonium salt, preferably ammonium sulfate which is used to increase the efficacy of the formulation.

However, it should be observed that EP 498.145 discloses a granulate composition and not a powder composition as the present invention does.

According to the description of the reference, the process for preparing the granular composition comprises reacting an acid acceptor with glyphosate or using glyphosate directly; mixing the solid alkyl glucoside or alkyl polyglucoside and ammonium sulfate in order to prepare a pasty mixture and thereafter granulating, extruding or spray drying to prepare said solid composition. On the other hand, the present application discloses a powder formulation which is not submitted to a granulation process. Besides, said patent does not try to optimize the ratio of ammonium sulfate to glyphosate acid as the present invention. This is illustrated by the use of an ammonium sulfate concentration from 20% to 80%. A concentration of 20% in the formulation is below the optimal and more than 30% serves no useful purpose. Without optimization of the ammonium sulfate to glyphosate ratio one cannot have in situ preparation of the soluble glyphosate salt nor maximize the concentration of glyphosate in the formulation.

Consequently the patent does not describe in situ production, while the present invention discloses one and the concentrations of glyphosate acid active ingredient described in said patent are much lower than the concentrations achieved in the present invention. Moreover, the surfactant adjuvant judiciously selected by the applicant is not a substance derived from glycoside or polyglycoside.

Actually, according to the present invention, the suitable surfactants specially selected for high efficiency, low toxicity as well as to act as an agglomerating agent for herbicide powder particles are liquid fatty acid amide derivatives which have high efficiency, low toxicity and are inexpensive.

U.S. Pat. No. 6,228,807 discloses a dry water-soluble agricultural acceptable herbicidal composition, which can be prepared as a water soluble powder form comprising N-phosphonomethylglycine or a water soluble salt of N-phosphonomethylglycine. It describes the use of at least one surfactant which in its form is liquid at 25° C. Actually it describes the use of any liquid surfactants, such as, nonionic, anionic, cationic and amphoteric ones. The surfactant gels in water and enhances the bioefficacy having less than about 5% by weight of water.

According to this document, the salt is prepared by a separate operation and not in situ in the water tank. The purpose of the invention is not related to obtaining a reduction of the amount of glyphosate active ingredient to be applied on the field by an increase in efficacy of the formulation. Ammonium sulfate is mentioned as an adjuvant, but there is no indication of ammonium sulfate being used to increase the efficacy of the formulation, because this is not the purpose of the patent. Consequently the amount of ammonium sulfate required in order to obtain an increase in efficacy is not mentioned nor is there any indication of an optimum ratio of ammonium sulfate to glyphosate acid which leads to a 30% increase in efficacy in the field. An increased efficacy is not sought after since this is not the objective of the U.S. Pat. No. 6,228,807 patent or a researched result. The herbicide composition contains any type of surfactant. This means that this US patent does not aim to improve its composition by choosing a specific surfactant. The document does not mention a judicious selection of a surfactant adjuvant. Ethoxylated coco amine is mentioned in the description but this is completely different from the surfactants used in the present application which specifically excludes the use of this compound because of its toxicity. Thus the product described in the patent is more toxic than the formulation of the present invention and the higher efficacy is not sought after since this is not the object of the patent.

WO 2010/053385 A1 discloses a liquid, homogeneous composition comprising a water-soluble glyphosate salt and a mixture of adjuvants including at least one surfactant, ammonium sulfate, at least one carboxylic acid preferably citric acid and a mixture of compatibilising substances preferably glycol and triethanolamine. While the purpose of the invention is to increase the efficacy of glyphosate, no reference is made to optimization of the ratio of ammonium sulfate to glyphosate and the suggested concentration of ammonium sulfate is twice the amount required by the present invention. The formulation described in this patent is entirely different from the composition object of the present invention, being a liquid instead of a powder, and using a water soluble salt instead of glyphosate acid.

The liquid form creates the need to add the carboxylic acid in addition to the two compatibilising substances in order to stabilize the formulation while the powder formulation does not require the addition of any of these three substances.

The liquid composition also requires the prior preparation of the glyphosate salt by a separate operation which increases the cost of the formulation, while for the powder formulation described in the present invention this is not required since the glyphosate salt is prepared in situ in the water tank. Furthermore because of the limited solubility of ammonium sulfate in water the use of a liquid formulation limits the concentration of the glyphosate active ingredient in the formulation to a value well below—approximately half—of that which is achieved with a powder.

U.S. Pat. No. 5,118,338 refers to a water soluble powder or granular free flowing glyphosate formulation and a surfactant that is a powdery or granular non-ionic polyglycol ether of a straight chain, saturated, high molecular weight fatty alcohol having an average chain length of $C_{16}$-$C_{18}$, about 25 units of ethylene oxide per mole of fatty alcohol and an HLB value of about 16. Suitable penetrating agents, such as, ammonium sulfate can be used. The patent envisages exclusively the use of a solid surfactant while the present invention envisages only liquid surfactants which are less expensive, less toxic and more efficient.

The patent uses polyglycol ethers that are produced by ethoxylation and therefore contain 1,4-dioxane which is a carcinogen while the present invention rejects this type of surfactant. In addition, the patent discloses the use of other additives in the form of liquids that may be added in minor amounts as long as they do not change the physical free flowing character of the formulation.

Thus, according to the patent referenced above, ammonium sulfate is one of the possible additives that can be included into the formulation, while in the present invention, ammonium sulfate is a critical ingredient, the new herbicide composition of the present invention being characterized by a judicious selection and a very narrow range concentration of its components.

The solid polyglycol ether is simple to incorporate in a powder formulation while the specific liquid surfactant that is used in the product of the instant invention is far more difficult to incorporate in a powder formulation. Moreover, the surfactant adjuvant judiciously selected by the applicant of the present invention is not a substance derived from polyglycol ether.

While ammonium sulfate is contemplated as an adjuvant for increase of efficacy, the optimum ratio of ammonium sulfate to glyphosate is not an object of the research and the concentration of ammonium sulfate is much higher than required. The consequence is that in situ preparation of the soluble glyphosate salt of the reference patent is not possible, since no space is left in the formulation for a solubility agent in order to form the soluble glyphosate salt in situ in the water tank.

DETAILED DESCRIPTION OF THE INVENTION

The present invention is related to a new water soluble powder glyphosate herbicide composition which aims to optimize efficiency and to minimize costs and toxicity. Said composition is characterized by a judicious selection of its components and a very narrow range of specific ingredients of components.

The present invention discloses a single packaged readied in situ water soluble powder glyphosate herbicide composition, consisting of an activator as a supplier of ammonium ions, a solubility agent as a supplier of cations for formation of a soluble glyphosate acid salt, a liquid surfactant and an antifoam agent all the components being in a very precise narrow range of weight ratios with respect to glyphosate.

According to the instant invention, the inorganic ammonium salts that can be used as a supplier of ammonium ions and their respective weight ratios to the pure (100%) glyphosate acid content of the formulation are the following: ammonium nitrate 57 parts with a lower limit of 53 parts and an upper limit of 61 parts of salt to 100 parts of pure (100%) glyphosate acid; ammonium chloride 38 parts with a lower limit of 35 parts and an upper limit of 41 parts of salt to 100 parts of pure (100%) glyphosate acid; ammonium carbonate 34 parts with a lower limit of 32 parts and an upper limit of 36 parts of salt to 100 parts of pure (100%) glyphosate acid; ammonium bicarbonate 56 parts with a lower limit of 52 parts and an upper limit of 60 parts of salt to 100 parts of pure (100%) glyphosate acid; mono ammonium phosphate 82 parts with a lower limit of 77 parts and an upper limit of 87 parts of salt to 100 parts of pure (100%) glyphosate acid, di ammonium phosphate 47 parts with a lower limit of 44 parts and an upper limit of 50 parts of salt to 100 parts of pure (100%) glyphosate acid, tri ammonium phosphate 35 parts with a lower limit of 33 parts and an upper limit of 37 parts of salt to 100 parts of pure (100%) glyphosate acid, ammonium sulfate 47 parts with a lower limit of 44 parts and an upper limit of 50 parts of salt to 100 parts of pure (100%) glyphosate acid. Ratios below the minimum decrease the efficacy of the formulation. Ratios above the maximum can be used but serve no useful purpose and decrease the concentration of glyphosate acid in the powder formulation.

Ammonium sulfate is the preferential ammonium salt.

Suitable solubility agents that can be used as a supplier of cations and their respective weight ratios to the pure (100%) glyphosate acid content of the formulation are the following: sodium carbonate 38 parts with a lower limit of 35 parts and an upper limit of 40 parts of salt to 100 parts of pure (100%) glyphosate acid, sodium bicarbonate 59 parts with a lower limit of 55 parts and an upper limit of 63 parts of salt to 100 parts of pure (100%) glyphosate acid, potassium carbonate 49 parts with a lower limit of 46 parts and an upper limit of 52 parts of salt to 100 parts of pure (100%) glyphosate acid, potassium bicarbonate 70 parts with a lower limit of 66 parts and an upper limit of 74 parts of salt to 100 parts of pure (100%) glyphosate acid, ammonium carbonate 34 parts with a lower limit of 32 parts and an upper limit of 36 parts of salt to 100 parts of pure (100%) glyphosate acid, ammonium bicarbonate 56 parts with a lower limit of 52 parts and an upper limit of 60 parts of salt to 100 parts of pure (100%) glyphosate acid, sodium hydroxide 29 parts with a lower limit of 27 parts and an upper limit of 31 parts of hydroxide to 100 parts of pure (100%) glyphosate acid, potassium hydroxide 39 parts with a lower limit of 36 parts and an upper limit of 42 parts of hydroxide to 100 parts of pure (100%) glyphosate acid. Ratios below the minimum lead to incomplete or slow dissolution of the glyphosate acid in the water tank. Ratios above the maximum can be used but serve no useful purpose and decrease the concentration of glyphosate acid in the powder formulation.

Sodium carbonate is the preferential solubility agent.

The appropriate liquid surfactant is selected among the fatty amide derivatives, particularly among coco amide derivatives, the minimum weight ratio of surfactant to the pure (100%) glyphosate acid content of the formulation being 7 parts of surfactant and the maximum 8 parts of surfactant to 100 parts of pure (100%) glyphosate acid. Ratios below the minimum decrease spreading and retention of the herbicide on the plant leaf. Ratios above the maximum can be used but serve no useful purpose and decrease the concentration of glyphosate acid in the powder formulation.

The main technical feature of the present invention consists in selecting an optimum amount of ammonium salt that acts as an ammonium ion donor, as the activator for glyphosate; selecting the most efficient surfactant, which must be also the least toxic and the most compatible with ammonium salt; said surfactant must also act as an agglomerating agent for powder particles; and the least expensive and most convenient solubility agent from the point of view of manufacture of the powder.

According to the present invention, the amount of ammonium salt, particularly of ammonium sulfate, in the composition is a critical parameter. It is important to keep this amount in the composition to the minimum quantity necessary in order to attain the 30% gain in efficacy so as to maximize the concentration of glyphosate acid in the composition and allow for the introduction in the composition of a solubility agent so as to be able to prepare the soluble salt of glyphosate in the water tank avoiding prior preparation by a separate operation.

Extensive field tests confirmed that there is indeed a very narrow optimal dosage range of ammonium salt, that is, the amount which corresponds to the maximum reduction in glyphosate acid requirement and below which the reduction is lesser and above which there is no additional gain.

Because the glyphosate molecules must crowd out the molecules of PEP in order to be successful, the efficiency of a glyphosate herbicide formulation is determined by the amount of active ingredient which enters the plant leaf in the shortest time. It is not the amount of herbicide applied on the field which counts, but the proportion which quickly penetrates into the leaf and diffuses through the cuticle.

Figure 1:
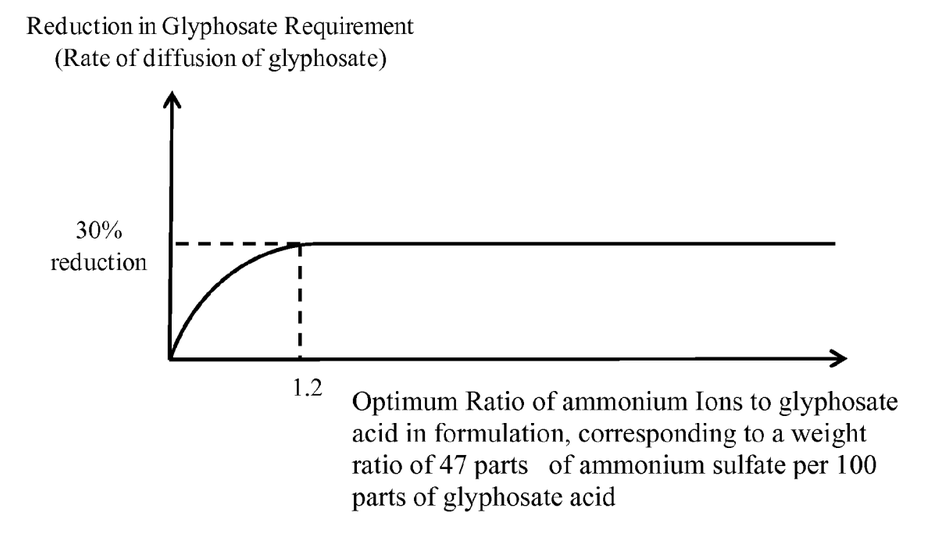
FIG. 1 depicts the effect of ammonium ions (expressed as a molar ratio to glyphosate acid) on the efficiency of the herbicide formulations disclosed herein

Glyphosate diffusion through the cuticle is enhanced by a less dissociated glyphosate molecule. The effect of ammonium ions upon glyphosate dissociation suggests that there is an optimum concentration of ammonium ions, that is, too little ammonium salt will lead to a low rate of penetration/diffusion while too much ammonium salt is useless and will not increase the rate of penetration/diffusion any further. Therefore one can expect a relationship between the rate of penetration/diffusion of glyphosate in the cuticle and the required amount of ammonium salt, such as ammonium sulfate as shown in FIG. 1 annexed, the reduction in the amount of glyphosate required in the formulation being proportional to the rate of penetration/diffusion of glyphosate into and through the leaf cuticle.

The optimum dosage of ammonium salt, that is, the smallest amount of ammonium salt which leads to the 30% gain in efficacy, was determined by using different ratios of ammonium sulfate to glyphosate and applying them on the field.

Having determined this optimal ratio, the development of the formulation composition began with glyphosate acid and ammonium salt in a precisely defined proportion.

It is important not to use more ammonium salt than the absolute minimum required so as to be able to maximize the concentration of glyphosate acid in the formulation and leave space for the glyphosate solubility agent. This is why one of the main technical features of the present invention consists in determining this optimum amount of ammonium sulfate that acts as an ammonium ion donor for activation of glyphosate.

On a molecular basis this optimum ratio of ammonium ions ($NH_4^+$) to pure glyphosate acid turns out to be around 1.2/1.0 (+/−7%) corresponding to a range of 0.12 to 0.135, weight/weight. For ammonium sulfate this translates to a range of 44 to 50 parts of ammonium sulfate to 100 parts of pure (100%) glyphosate acid. A weight ratio of 0.44 to 0.50 of ammonium sulfate to pure glyphosate acid leaves space for other components making it easy to include other components and consequently opens the possibility to create a different and commercially viable formulation.

Extensive field tests showed that the optimal ratio is in the range of 44 to 50 parts in weight of ammonium sulfate to 100 parts of the pure (100%) glyphosate acid content of the formulation The use of less ammonium sulfate diminishes the activation effect. The use of a higher amount does not lead to an increased activation effect but will decrease the concentration of glyphosate acid in the soluble powder due to the added amount of ammonium salt.

This optimal ratio of ammonium ions to glyphosate leads to a reduction of 30% in the required amount of glyphosate which needs to be applied on the field.

Many glyphosate herbicides use ammonium sulfate as an activator but only the determination of the optimum amount of ammonium sulfate required leads to the possibility of designing a solid powder formulation with a very narrow range of specific ingredients of composition so as to present simultaneously all the desired properties of greatly increased efficacy, in situ preparation of the salt in the water tank, low toxicity and high content of the glyphosate active ingredient.

It was the important discovery that there exists an optimum dosage of ammonium ions and consequently of ammonium salt which opened the possibility of conceiving a soluble powder glyphosate formulation with the highest possible concentration of glyphosate active ingredient, with the inclusion of a solubility agent for in situ production of the soluble glyphosate salt in the water tank, while securing a 30% gain in efficacy when compared to the standard liquid formulation.

According to the present invention, the amount of ammonium sulfate in the composition is a critical parameter. It is important to keep this amount in the composition to a minimum quantity necessary in order to attain the 30% gain in efficacy and at the same time maximize the concentration of glyphosate acid in the formulation and allow for the introduction in the formulation of a solubility agent so as to be able to prepare the soluble salt of glyphosate in the water tank avoiding prior preparation by a separate operation.

The objective was to develop a low cost but highly efficient glyphosate herbicide formulation by use of the optimal amount of ammonium ions together with a compatible surfactant and the optimal amounts of the other ingredients.

All glyphosate herbicides must contain a surfactant in order to increase retention and lower surface tension in order to increase spreading of the pesticide on the leaf.

The most commonly used surfactant in 360 g/liter liquid formulations is fatty amine ethoxylate. This surfactant is now widely recognized as being toxic presenting a high risk of damage to the eyes, high toxicity to aquatic organisms and daphnia and a high content of 1,4-dioxane which is carcinogenic.

Because of this, the researchers rejected the use of this surfactant and searched for other surfactants which have the same efficiency but are less toxic, are fully compatible with ammonium sulfate and are inexpensive. Furthermore because the formulation is in the form of a powder it was required that the surfactant also act as an agglomerating agent binding together the smallest particles in the powder so as to avoid the presence of fines in the final product.

The efficacy of ammonium sulfate is dependent on the type of surfactant. The ideal surfactant must maximize the spreading and retention effect, have low toxicity, low cost and be compatible with ammonium sulfate.

So, the present invention involves yet another very important condition concerning the herbicide composition. The applicant discovered that coco amide surfactants, which are liquids, were particularly efficient. They are appropriate to be used since they are, at the same time fully compatible with ammonium sulfate, more efficient, cheaper and less toxic than most solid surfactants commonly used in powder formulations. Moreover, they act as an agglomerating agent for fines in the powder formulation.

The preferred and most effective surfactants are coco amide derivatives. They are, among the least toxic surfactant products for use with glyphosate, just as efficient as fatty amine ethoxylates and have the best performance and compatibility with ammonium sulfate. Particularly preferred are coco amide amine derivatives, preferably, N-alkyl coco amide amine derivatives such as, coco amide propyl amine oxide and coco amide propyl betaine. The two chosen surfactants have all of those characteristics being 15 times less toxic for fish and 100 times less toxic for daphnia when compared to a fatty amine ethoxylate. Also they do not contain 1,4-dioxane and hold no risk of eye damage.

The toxicological advantage of coco amide propyl amine oxide surfactant with respect to fatty amine ethoxylate is shown on the following table:

| TEST | Coco amide propyl amine oxide | Fatty amine ethoxylate |
| --- | --- | --- |
| Fish toxicology $LC_{50}$ (mg/l) OECD 203.96h | 6 | 0.42 |
| Acute daphnia immobilization $EC_{50}$ (mg/l) OECD 202 | 45 | 0.46 |
| Biodegradability (%) | >90 | <60 |
| Acute oral toxicology $LD_{50}$ (mg/kg) rats | >2000 | 200-2000 |
| Eye irritation rabbits | Irritant | Serious eye damage |
| 1,4-Dioxane content (carcinogen) | — | Up to 25,000 ppm |

The inevitable presence of 1,4-dioxane in all ethoxylated products is the reason why all ethoxylates including coco amide ethoxylates were excluded from consideration in the product of the present invention.

However this choice of the ideal surfactant with all the desired characteristics of low toxicity, low cost, high efficiency regarding spray retention, spreading and compatibility with ammonium sulfate when used in a powder formulation lead to a manufacturing problem as described further on, which was an additional obstacle the researchers had to overcome in order to achieve the combination of all the ideal constituents of a powder formulation.

The high performance and low toxicity of coco amide propyl amine oxide makes it the preferred choice. Coco amide propyl betaine was tested and is just as efficient and also has low toxicity, however it is sometimes more expensive than the amine oxide.

Coco amide derivatives are commonly sold as liquid solutions in water usually with a concentration of 30% of active ingredient.

A higher concentration is advantageous both for the manufacturing process and for the final composition of the powder formulation, since less water in the surfactant solution leads to a drier powder and greatly simplifies the manufacturing process. A surfactant solution of especially high concentration, in the range of 80% to 90% in weight, preferably 87% in weight, was developed for use in the soluble powder object of this invention. The use of this concentrated surfactant solution led to a great reduction in powder humidity and a 100% gain in productivity of the manufacturing equipment when compared to use of the standard 30% surfactant solution.

Therefore in a particular embodiment of the instant invention, coco amide derivative, preferably a N-alkyl coco amide derivative, such as, coco amide propyl amine oxide, is present as a water solution in a ratio of 80 to 90% in weight of coco amide.

Since coco amide derivatives foam when in contact with water it is necessary to add a minute amount of an antifoam agent with a weight ratio between 0.05 parts and 0.06 parts per 1.0 part of surfactant active ingredient, which corresponds approximately to 0.2% (two tenths of one percent) of the total weight of the soluble powder. Diverse anti foam agents were tested. For instance SAG 1572 Momentive, DSP and Q2-5211 Dow Corning were tested and shown to be satisfactory.

Current practice for liquid glyphosate formulations is the use of 10 parts of surfactant to 100 parts of the pure (100%) glyphosate acid content of the formulation. However, field tests have shown that the use of coco amide derivatives, particularly coco amide propyl amine oxide, can be reduced by 20% and that a ratio of 8 parts of surfactant to 100 parts of pure glyphosate acid is sufficient.

The formulation therefore uses a weight ratio of coco amide derivative/pure Glyphosate Acid=8/100=0.08. Ratios below 0.07 make for a less efficient product. Ratios above 0.08 serve no useful purpose and decrease the concentration of glyphosate acid in the formulation.

Another particular aspect of the present invention is the one related to the physical form of the herbicide composition. According to the invention, only a powder or granule form allows simultaneously for the maximization of the glyphosate concentration, the use of ammonium sulfate without a stabilizer and in situ preparation of the soluble glyphosate salt. However a coco amide derivate water solution surfactant cannot be incorporated in the preparation of a granule but only in a powder.

As far as a skill in the art knows, no powder formulation has ever attempted to use this liquid surfactant, because its inclusion in the powder is a difficult and inconvenient operation, all the more so if sodium carbonate is present in the formulation which is a requirement for in situ preparation of glyphosate salts.

The present invention also aims to prepare the soluble salt of glyphosate in situ by incorporating a solubility agent in the powder for preparation of the soluble glyphosate salt in the water tank.

Glyphosate acid is insoluble in water and must be transformed into a salt in order to dissolve in the water tank upon use. Having determined that the composition is a powder the next step was to choose the best solubility agent in order to form a soluble glyphosate salt when in contact with water.

Known solid solubility agents for glyphosate are alkali carbonates, bicarbonates and hydroxides such as sodium carbonate, potassium carbonate and ammonium carbonate and their respective bicarbonates and hydroxides, which when added to the glyphosate acid in the powder will produce, when in contact with water, the corresponding water soluble alkali salts of glyphosate. Sodium carbonate is the alkali salt with the lowest cost and is more convenient to handle and incorporate in the powder than the hydroxide and was, therefore, the solubility agent of choice.

Formation of the soluble glyphosate salt in situ avoids the need to produce the glyphosate acid salt by a separate operation prior to formulation as is the case for the standard 360 g/liter formulation which consists of the isopropyl amine salt and therefore requires amination of glyphosate acid for production of the salt prior to use in the formulation.

As the powder gets in contact with water, sodium carbonate dissolves liberating carbon dioxide and forming sodium hydroxide which reacts with the glyphosate acid forming the soluble sodium salt.

The theoretical ratio for this reaction is 32 parts of sodium carbonate to 100 parts of the pure (100%) glyphosate acid content of the formulation.

In order to ensure immediate solubility of the glyphosate acid in water an excess of sodium carbonate over the theoretical amount is recommended which was determined by testing and the formulation uses an excess of 10% to 25% which translates into a weight ratio of Sodium Carbonate/Pure Glyphosate Acid between 0.35 and 0.40. A ratio below 0.35 may lead to a small amount of non-reacted glyphosate acid at the bottom of the water tank while a ratio above 0.40 serves no useful purpose and decreases the concentration of glyphosate acid in the powder.

The same result can be achieved using other alkali salts such as for instance potassium or ammonium carbonates and bicarbonates or hydroxides, but they are significantly more expensive than sodium carbonate, and either require the use of more product in order to dissolve the glyphosate acid and therefore lead to a lower concentration of glyphosate in the formulation, or are difficult to incorporate in the powder without having a corresponding advantage.

According to the present invention, the herbicide composition is presented as a powder. It shows significant advantages over both liquid solutions and granules.

Because of the limited solubility of ammonium sulfate in water, liquid solutions cannot be prepared with a pure glyphosate acid content as high as in a powder.

For instance one cannot dissolve more than 25% of the required amount of ammonium sulfate necessary in order to attain the 30% increase in efficacy in the standard 360 g/liter liquid solution formulation.

Furthermore in order to stabilize a liquid formulation containing ammonium sulfate it is necessary to introduce other chemicals such as illustrated for instance in WO2010/053385 A1. This problem was overcome by using a powder formulation in the present invention.

A powder has other significant advantages with respect to a liquid formulation:

Transport of a smaller amount of powder compared to a larger amount of liquid.

The freight for transport of a liquid in flasks is more expensive than the transport of a powder packed in plastic bags.

The flask for a liquid is more expensive than the plastic bag used to pack the powder.

It is more convenient for the farmer to unload the contents of a plastic bag into the water tank than to discharge the standard 20 liter flask of liquid.

In case herbicide packing must be returned for destruction the cost of freight for the return of empty flasks is more expensive than the return of empty plastic bags.

Presentation in the form of a granule requires a much higher investment than for a powder and it is virtually impossible to incorporate a coco amide propyl amine oxide water solution into a granule.

The disadvantages commonly attributed to soluble powders are the formation of fines which float in the air when the bags are discharged into the water tank and that powders often float on the surface of the water in the tank.

The disadvantages described above are overcome by the invention of the instant application.

Because the specific gravity of all the components of the powder is much higher than the specific gravity of water, the powder doesn't float but sinks immediately and dissolves in the tank. Formation of fines is avoided by the use of the specific surfactant selected by the applicant, which agglomerates the fines and by an adequate milling procedure for the ammonium sulfate.

It is the simultaneous use of all the technical features previously described, that leads to the novel results and not any one single individual characteristic.

The present invention is also related to a process to prepare a single packaged ready to use soluble powder herbicide composition.

Because of the nature of the surfactant the present invention required special mixing equipment to prepare a single packaged readied in situ glyphosate soluble powder herbicide composition. This is because the incorporation of a liquid coco amide derivate surfactant, such as, coco amide propyl amine oxide or coco amide propyl betaine, in a powder leads to a significant difficulty in the manufacturing process.

As the coco amide surfactant solution comes into contact with the mixture of solids—glyphosate, ammonium sulfate and sodium carbonate—there forms immediately a sticky gum at the point of contact between the liquid and the solid. This gum must be broken up and mixed with the solids in order to constitute a homogeneous product. Common mixing equipment such as a vertical helix or screw mixer or a ribbon blender will not do the job.

The manufacturing process begins with milling the ammonium sulfate in a standard stainless steel mill so as to obtain the same particle size as the glyphosate and the sodium carbonate particles. A different particle size leads to segregation of the larger particles in the powder and therefore to a non-homogeneous product.

The three solids are then mixed and the surfactant is sprayed on to the solids placed in a ribbon blender with intense mixing during the spraying process. Introduction of the solids in the mixer must be done in a given order, either carbonate, glyphosate and sulfate or sulfate, glyphosate and carbonate. Sulfate and carbonate should not be introduced one after the other for there will result emanation of ammonia. The spray must produce a veritable fog of liquid. This is achieved either by using 0.5 mm spray nozzles, or with larger nozzles and compressed air so that the liquid is exploded into very fine droplets over the ribbon blender.

Many nozzles are used so that the spray fog covers uniformly the surface of the ribbon blender.

However the spray by itself is still insufficient in order to obtain a homogeneous product since what is now achieved is an immense quantity of tiny sticky gum particles which must be broken up in order to obtain a homogeneous powder. In order to achieve this, the ribbon blender must be equipped with an extra high speed mixer known as an intensifier placed at the bottom of the blender. The intensifier consists of three or more small rotating star shaped knives each one of slightly larger diameter than the previous one, all of them attached to a high speed (1800 rpm to 3600 rpm) rotating axis, forming a small cone like agitator, the borders of the cone being the cutting edges of the star shaped knives. Air must be injected around the intensifier so that high speed rotation is achieved in the slightly fluidized mass of solids around the intensifier. As the ribbon blender repeatedly brings the solid mass around towards its center, the solids come into contact with the intensifier at the bottom of the mixer which breaks up the minute particles of gum.

Since the surfactant comes in a water solution an exothermic reaction takes place upon contact of the liquid and the solids. Cooling must therefore be provided either by a jacket around the ribbon blend mixer or by air injection at the bottom of the mixer. If the temperature rises above 50° C. the solids will form a brick like structure which will stop the mixing process.

Liquid spraying is best conducted in an intermittent fashion with one or two minutes of spraying with mixing interspersed by three or four minutes of mixing without spraying. The particle size of the solids is not affected by the entire process being the same in the finished powder as in the initial ingredients.

The applicant determined that using the special 80% to 90% in weight of coco amide propyl amine oxide water solution in place of the standard 30% solution, one could avoid the exothermic reaction and greatly speed up the entire manufacturing process leading to a very significant gain in productivity. A thirty minute manufacturing cycle using the 30% surfactant water solution is cut in half by using the 87% concentrated solution which allows for continuous injection of the liquid. Also the humidity of the powder is reduced from around 9% using the 30% surfactant water solution to 1% to 2% using the 87% concentrated solution which greatly improves the flowability of the powder.

Despite the difficulties concerning the use of a liquid surfactant in a powder formulation, by far the most important technical aspect to be solved, is to determine the very narrow range of specific ingredients of composition.

According to preferential embodiment of the present invention, the ready to use glyphosate herbicide water soluble powder composition comprises an amount of technical glyphosate and a very narrow range of specific adjuvants, in a mixture of:

a—an activator supplier of ammonium ions that is ammonium sulfate in a ratio of 44 to 50 parts in weight of ammonium sulfate to 100 parts of the pure (100%) glyphosate acid content of the formulation;

b—a solubility agent that is sodium carbonate in a ratio of 35 to 40 parts in weight of sodium carbonate to 100 parts of the pure (100%) glyphosate acid content of the formulation;

c—a liquid surfactant agent in an 80 to 90% in weight water solution of coco amide propyl amine oxide and in a ratio of 7 to 8 parts in weight to 100 parts of the pure (100%) glyphosate acid content of the formulation;

d—an antifoam agent in a ratio of 5 to 6 parts in weight to 100 parts of coco amide derivate surfactant.

In this preferred embodiment of the invention and according to the concepts of the present invention, the composition of the ingredients used for the manufacture of the herbicide water soluble powder composition can be described as follows on a dry basis (excluding the water brought into the formulation with the liquid surfactant solution):

Active Ingredient—Pure (100%) Glyphosate Acid 490 g/kg to 530 g/kg;
Activator—Ammonium sulfate 246 g/kg to 234 g/kg;
Solubility agent—Sodium carbonate 202 g/kg to 186 g/kg;
Surfactant—Coco amide propyl amine oxide—40 g/kg to 37 g/kg;
Antifoam—1.5 g/kg to 2.0 g/kg;
Glyphosate impurities from zero to 29 g/kg.

A concentration of ammonium sulfate, sodium carbonate or surfactant above the higher limits indicated can be used but serves no useful purpose and will lower the concentration of glyphosate acid in the formulation, while concentrations below those limits will decrease the efficacy of the formulation.

Despite the fact that the individual components of the applicant composition are well known in the art and have already been used along with glyphosate, it is the simultaneous use of all of them together in a very precise proportion which leads to the novel results, the formulation being characterized by the fact that the ingredients for its manufacture are comprised in a very precise narrow range of ratios with respect to glyphosate. This is due to the main technical feature of the present invention which consists in determining the exact optimum amount of ammonium sulfate acting as a supplier of ammonium ions; selecting the most efficient surfactant, which is the least toxic and the most synergistic with ammonium sulfate; said surfactant also acting as an agglomerating agent for fine powder particles.

The powder formulation which results from the discovery that there is an optimum amount of ammonium sulfate for maximum efficacy, is a unique herbicide which because of the very narrow amount of the specific ingredients of the composition presents a 30% increase in efficacy when compared to other known formulations, particularly the standard 360 g/liter liquid formulation, which does not require previous preparation of the soluble glyphosate salt by a prior separate operation, has a low toxicity, has a high content of the glyphosate active ingredient, has a low industrial cost, a proven manufacturing process and is most economical to manufacture, transport, handle, store and package, all together in a single readied in situ formulation which constitutes a unique novel product not described in the literature nor commercially existent.

There is no known glyphosate formulation with this precise combination of ingredients possibly because the optimum amount of ammonium ions for maximum efficacy has not been previously determined and because liquid coco amide amine derivatives have not been previously incorporated for use as a surfactant in powder formulations.

The remarkable efficacy of this formulation which was tested on a large scale on the field will result in a 30% decrease in the use of glyphosate herbicides which will have a most beneficial effect on the environment, on the amount of pesticide residue remaining on the crop and on the cost of food.

Examples of Experimental Results

The product was extensively tested on the field. During eighteen months the soluble powder formulation was applied in different dosages on a variety of weeds in the state of Parana, Brazil and in the province of Cape Town in the Republic of South Africa and the results were compared with those obtained applying the standard product 360 g/liter liquid formulation side by side on the same fields.

The extensive testing in Brazil and South Africa confirmed the efficacy of the product and showed an average gain of 30% in the efficacy of the soluble powder formulation object of the present invention when compared to the standard product 360 g/liter liquid formulation More than one hundred field tests of the Soluble Powder were carried out. Each test consisted in applying different dosages of glyphosate acid on the field using the Soluble Powder object of the present invention and similar dosages of the standard 360 g/liter liquid formulation and comparing the results obtained side by side on the same field. Phytotoxicity of the weeds was measured by sampling and visual counting. All results were recorded and photographs taken before and after the tests.

The following examples show typical experimental results obtained with the Soluble Powder object of the invention and comparison with the results obtained with the standard 360 g/liter soluble liquid solution. These examples illustrate but do not limit the present invention.

In these examples the ingredients used to manufacture the Soluble Powder product had the composition showed in Table 1. Whether the 30% or the 87% water solutions of surfactant are used does not affect the efficacy of the powder which depends only upon the composition on a dry basis.

TABLE 1

COMPOSITION OF THE SOLUBLE POWDER FORMULATION INGREDIENTS

| Ingredients | Based upon 100 parts in weight of glyphosate acid | Weight % dry basis | Weight % wet basis 30% solution | Weight % wet basis 87% solution |
|---|---|---|---|---|
| Glyphosate acid 100% | 100 | 50.5% | 46.1% | 50.1% |
| Impurities in Technical Glyphosate 97.3% | 2.78 | 1.4% | 1.3% | 1.4% |
| Glyphosate technical 97.3% | 102.78 | 51.9% | 47.4% | 51.5% |
| Sodium carbonate | 40 | 20.2% | 18.4% | 20.1% |
| Ammonium sulfate | 47 | 23.7% | 21.7% | 23.6% |
| Coco amide propyl amine oxide (100%) | 8 | 4.0% | 3.7% | 4.0% |
| Antifoam | 0.44 | 0.2% | 0.2% | 0.2% |
| Total dry basis | 198.22 | 100.0% | 91.4% | 99.4% |
| Water with Surfactant 30% or 87% solutions | 18.7 (30%) 1.2 (87%) | | 8.6% | 0.6% |
| Total | 216.92 (30%) 199.43 (87%) | | 100.0% | 100.0% |

Because of weight loss due to the reaction between the water and sodium carbonate the end product resulting from use of the 30% surfactant solution had a pure (100%) glyphosate acid content of 497 g/kg.

In view of the 30% gain in efficacy, normal product usage of this formulation is 0.50 kg (containing 250 g/kg of pure glyphosate acid) in place of 1.0 liter of the 360 g/liter liquid solution.

The comparison between the Soluble Powder and the 360 g/liter formulation is made based upon the amount of glyphosate acid which was applied on the field expressed in grams of glyphosate acid per hectare.

This is obtained by multiplying the amount of product applied on the field by the concentration of the product (g/l for the liquid solution and g/kg for the Soluble Powder).

For instance applying 4.0 liters per hectare of the 360 g/l liquid solution corresponds to:

4.0 l/ha×360 g/l=1440 g/ha of glyphosate acid applied on the field.

Applying 2.0 kg/ha of Soluble Powder made using the 30% surfactant water solution corresponds to:

2.0 kg/ha×497 g/kg=994 g/ha of glyphosate acid applied on the field.

The number appearing in the column DAA (Days After Application) is the phytotoxicity of the product to the weed being tested, a value above 80% being considered as a satisfactory result.

Example 1

Place: Field Station at Faculdade Integrado de Campo Mourão, State of Paraná, Brazil
Plantation—Experimental field of weeds
Weed (*Brachiaria decumbens*—perennial grass)
Stage of plant: 30 cm tall to Flowering

| Product | Glyphosate acid applied on field g/ha | Result 30 DAA |
|---|---|---|
| 360 g/l | 1440 | 90% |
| 360 g/l | 1800 | 100% |
| Soluble Powder | 1012 | 95% |
| Soluble Powder | 1265 | 100% |

The results show that in order to attain 100% phytotoxicity for *brachiaria decumbens* one can apply 100×(1−1265/1800)=30% less glyphosate acid using the Soluble Powder than using the standard 360 g/l liquid solution. Also in order to attain 95% phytotoxicity for *brachiaria decumbens* one can apply 100×(1−1012/1440)=30% less glyphosate acid using the Soluble Powder than using the standard 360 g/l liquid solution. Therefore in this experiment the Soluble Powder had an efficacy 30% above that of the standard 360 g/l standard liquid solution product.

Example 2

Place: Urai, State of Paraná, Brazil.
Citrus plantation
Weed (*Digitaria insularis*—perennial grass)
Stage of plant: up to 60 cm

| Product | Glyphosate acid applied on field g/ha | Result 35 DAA |
|---|---|---|
| 360 g/l | 720 | 66% |
| 360 g/l | 1080 | 93% |
| Soluble Powder | 754 | 86% |

The results show that in order to attain 86% to 93% phytotoxicity for *digitaria insularis* one can apply 100×(1−754/1080)=30% less glyphosate acid using the Soluble Powder than using the standard 360 g/l liquid solution. Applying comparable amounts of 720 g/ha in the form of the 360 g/liter liquid solution and 754 g/ha in the form of the Soluble Powder the latter has a satisfactory 86% efficacy while the result for the 360 g/liter SL is 66% which is below 80% and therefore unacceptable.

The 30% gain in efficacy of the Soluble Powder with respect to the 360 g/l liquid solution while observed in general is not observed for all weeds at all stages of weed growth, there being some weeds for which the gain in efficacy is much greater. On the other hand when weeds are very tall the gain in efficacy while still very significant is less pronounced. The next examples illustrate this.

Example 3

Place: Cambé, State of Paraná, Brazil
Apple plantation.
Weed *Richardia brasiliensis*—perennial grass.
Stage of plant: up to 60 cm

| Product | Glyphosate acid applied on field g/ha | Result 35 DAA |
|---|---|---|
| 360 g/l | 720 | 90% |
| 360 g/l | 360 | 75% |
| Soluble Powder | 423 | 90% |
| Soluble Powder | 611 | 90% |

The results show that in order to attain 90% phytotoxicity for *richardia brasiliensis* one can apply 100×(1−423/720)=41% less glyphosate acid using the Soluble Powder than using the standard 360 g/l liquid solution. Applying comparable amounts of 360 g/ha in the form of the 360 g/liter liquid solution and 423 g/ha in the form of the Soluble Powder the latter has a satisfactory 90% efficacy while the result for the 360 g/liter SL is 75%, that is, below the 80% threshold and therefore unacceptable.

Example 4

Place: Urai, State of Paraná, Brazil.
Citrus plantation
Weed (*Digitaria insularis*—perennial grass)
Stage of plant: up to 75 cm.

| Product | Glyphosate acid applied on field g/ha | Result 28 DAA |
|---|---|---|
| 360 g/l | 720 | 68% |
| 360 g/l | 1080 | 98% |
| 360 g/l | 1440 | 100% |
| Soluble Powder | 754 | 90% |
| Soluble Powder | 980 | 100% |

The results show that in order to attain 90% phytotoxicity for *digitaria insularis* one can apply 100×(1−754/1080)=30% less glyphosate acid using the Soluble Powder than using the standard 360 g/l liquid solution. In order to attain 100% phytotoxicity for *digitaria insularis* one can apply 100×(1−980/1440)=32% less glyphosate acid using the Soluble Powder than using the standard 360 g/l liquid solution. Applying comparable amounts of 720 g/ha in the form of the of 360 g/liter liquid solution and 754 g/ha in the form of the Soluble Powder the latter has a satisfactory 90% efficacy while the result for the 360 g/liter SL is 68% which is below 80% and therefore unacceptable.

Example 5

Place: Arapongas, State of Paraná, Brazil.
Coffee plantation
Weed: *Commelina benghalensis*—perennial
Stage of plant: 20 cm to Flowering.

| Product | Glyphosate acid applied on field g/ha | Result 40 DAA |
|---|---|---|
| 360 g/l | 1080 | 70% |
| 360 g/l | 1440 | 85% |
| 360 g/l | 1800 | 85% |
| Soluble Powder | 936 | 85% |
| Soluble Powder | 1292 | 90% |

The results show that in order to attain 85% phytotoxicity for *commelina benghalensis* one can apply 100×(1−936/1440)=35% less glyphosate acid using the Soluble Powder than using the standard 360 g/l liquid solution. In order to attain 90% phytotoxicity for *commelina benghalensis* one can apply 100×(1−1292/1800)=37% less glyphosate acid using the Soluble Powder than using the standard 360 g/l liquid solution. Applying comparable amounts of 1080 g/ha in the form of the 360 g/liter liquid solution and 936 g/ha in the form of the Soluble Powder the latter has an 85% efficacy while the result for the 360 g/liter soluble liquid is 70% which is below the 80% threshold and therefore unacceptable.

Example 6

Place: Cambe, State of Paraná, Brazil.
Apple plantation
Weed: *Cynodon dactylon*
Stage of plant: up to 60 cm.

| Product | Glyphosate acid applied on field g/ha | Result 40 DAA |
|---|---|---|
| 360 g/l | 720 | 50% |
| Soluble Powder | 611 | 75% |
| Soluble Powder | 870 | 85% |

The results show that applying 611 g/ha of glyphosate acid in the form of the Soluble Powder, phytotoxicity for *cynodon dactylon* was 50% higher than that attained applying 18% more glyphosate acid (720 g/ha) using the 360 g/l liquid solution.

Example 7

Place: Cambé, State of Paraná, Brazil.
Apple plantation
Weed: *Sida rhombifolia*
Stage of plant: up to 60 cm.

| Product | Glyphosate acid applied on field g/ha | Result 40 DAA |
|---|---|---|
| 360 g/l | 720 | 75% |
| 360 g/l | 1080 | 95% |
| Soluble Powder | 611 | 95% |
| Soluble Powder | 870 | 98% |

The results show that in order to attain 95% phytotoxicity for *sida rhombifolia* one can apply 100×(1−611/1080)=43% less glyphosate acid using the Soluble Powder than using the standard 360 g/l liquid solution. Applying 611 g/ha of glyphosate acid in the form of the Soluble Powder phytotoxicity for *sida rhombifolia* was 95% while applying 18% more glyphosate acid (720 g/ha) using the 360 g/l liquid solution, phytotoxicity was 75% below the 80% minimum and therefore unacceptable.

Example 8

Place: Field Station at Faculdade Integrado de Campo Mourão, State of Paraná, Brazil
Plantation: Experimental field of weeds
Weed *Digitaria insularis*—perennial grass
Stage of plant: Flowering 150 cm tall

| Product | Glyphosate acid applied on field g/ha | Result 30 DAA |
|---|---|---|
| 360 g/l | 1440 | 85% |
| 360 g/l | 1800 | 93% |
| Soluble Powder | 888 | 80% |
| Soluble Powder | 1187 | 88% |
| Soluble Powder | 1242 | 85% |

The results show that in order to attain 85% to 88% phytotoxicity for very tall *digitaria insularis* one can apply 100×(1−1187/1440)=18% less glyphosate acid using the Soluble Powder than using the standard 360 g/l liquid solution. It is not a usual agricultural practice to apply herbicide on such tall weeds. As the weed gets taller more and more pesticide must be applied and it is very significant that even under these extreme and unusual conditions the Soluble Powder formulation still shows an advantage.

Agricultural practice consists in applying herbicide on a field which has all kinds of weeds. While it is important to determine the phytotoxicity of a herbicide for each type of weed, the farmer is more interested in the overall result on a field of mixed weeds, which is why many tests were performed on fields presenting a mixture of different types of weeds.

Example 9

Place: Field Station Arapongas, State of Paraná, Brazil
Coffee plantation
Weeds: *Commelina benghalensis, bidens pilosa, sida rhombifolia, brachiaria plantaginea, digitaria horizontalis, alternanthera tenella, digitaria insularis* and others.
Stage of plant: 15 cm to flowering all stages mixed

| Product | Glyphosate acid applied on field g/ha | Result 40 DAA |
|---|---|---|
| 360 g/l | 1440 | 95% |
| Soluble Powder | 936 | 95% |

The results show that in order to attain 95% phytotoxicity for this field of mixed weeds one can apply 100×(1−936/1440)=35% less glyphosate acid using the Soluble Powder than using the standard 360 g/l liquid solution.

Example 10

Place: Cambé, State of Paraná, Brazil.
Apple plantation
Weeds: *Commelina benghalensis, cynodon dactylon, richardia brasiliensis, sida rhombifolia, alternanthera tenella*, and others.

Stage of plant: all stages mixed.

| Product | Glyphosate acid applied on field g/ha | Result 30 DAA |
|---|---|---|
| 360 g/l | 720 | 80% |
| 360 g/l | 1080 | 80% |
| 360 g/l | 1440 | 90% |
| Soluble Powder | 598 | 80% |
| Soluble Powder | 851 | 90% |

The results show that in order to attain 80% phytotoxicity for this field of mixed weeds one can apply 100×(1−851/1440)=40% less glyphosate acid using the Soluble Powder than using the standard 360 g/l liquid solution. Applying 720 g/ha glyphosate acid in the form of the 360 g/liter liquid solution and 598 g/ha in the form of the Soluble Powder the latter has the same efficacy when applied in a 17% lower dosage than that of the 360 g/liter formulation.

What is claimed is:

1. A powdered herbicide composition comprising glyphosate, an activator, a solubility agent, and a liquid surfactant agent,
    wherein the glyphosate is glyphosate acid;
    wherein the composition is water soluble;
    wherein the activator is an ammonium salt selected from the group consisting of ammonium nitrate, ammonium chloride, ammonium carbonate, ammonium bicarbonate, mono ammonium phosphate, di ammonium phosphate, tri ammonium phosphate, ammonium sulfate, and combinations thereof, providing ammonium ions within the range of from about 0.12 to about 0.135 parts by weight per 1.0 part by weight of pure (100%) glyphosate acid;
    wherein the solubility agent is an alkali salt or alkali hydroxide selected from the group consisting of sodium carbonate, sodium bicarbonate, potassium carbonate, potassium bicarbonate, sodium hydroxide, potassium hydroxide, and combinations thereof, present in an amount to provide from about 1.10 to about 1.25 mole alkali ion per mole glyphosate acid; and
    wherein the liquid surfactant agent is an aqueous solution of coco amide selected from the group consisting of coco amide propyl amine oxide, coco amide propyl betaine, and combinations thereof and is present within a range of from about 7 to about 8 parts by weight per 100 parts by weight of pure (100%) glyphosate acid.

2. The composition of claim 1, wherein the activator is ammonium sulfate and is present in a range of from about 44 parts to about 50 parts by weight per 100 parts by weight of pure (100%) glyphosate acid.

3. The composition of claim 1, wherein the solubility agent is sodium carbonate and is present in a range of from about 35 parts to about 40 parts by weight of sodium carbonate per 100 parts by weight of pure (100%) glyphosate acid.

4. The composition of claim 1, wherein the liquid surfactant is coco amide propyl amine oxide and is present in a range of from about 7 to about 8 parts by weight of pure surfactant per 100 parts by weight of pure (100%) glyphosate acid.

5. The composition of claim 1, wherein the liquid surfactant agent is aqueous solution of coco amide propyl amine oxide having a concentration of from about 80% to about 90% by weight coco amide propyl amine oxide.

6. The composition of claim 1, comprising at least about 500 g glyphosate acid active ingredient per kg of total composition.

7. A single package product containing the composition of claim 1.

* * * * *